United States Patent [19]

Dexter et al.

[11] 4,283,327

[45] Aug. 11, 1981

[54] 2-(2-HYDROXY-3,5-DI-TERT-OCTYL-PHENYL)-2H-BENZOTRIAZOLE STABILIZED COMPOSITIONS

[75] Inventors: Martin Dexter, Briarcliff Manor; Roland A. E. Winter, Armonk, both of N.Y.

[73] Assignee: Ciba-Geigy Corporation, Ardsley, N.Y.

[21] Appl. No.: 68,275

[22] Filed: Aug. 20, 1979

Related U.S. Application Data

[63] Continuation of Ser. No. 6391, Jan. 25, 1979, abandoned.

[51] Int. Cl.³ .......................... C08K 5/27; C08K 5/34
[52] U.S. Cl. .............................. 260/45.8 NT; 548/260

[58] Field of Search ................ 548/260; 260/45.8 NT, 260/22 A

[56] References Cited

U.S. PATENT DOCUMENTS

| | | | |
|---|---|---|---|
| 3,487,453 | 12/1969 | Sheehan | 8/100 |
| 4,041,044 | 8/1977 | White | 548/260 |

*Primary Examiner*—Paul M. Coughlan, Jr.
*Attorney, Agent, or Firm*—Luther A. R. Hall

[57] ABSTRACT

2-[2-Hydroxy-3,5-di-tert-octylphenyl]-2H-benzotriazole exhibits outstanding efficacy in protecting organic substrates from light induced deterioration as well as good resistance to loss by volatilization or exudation during the high temperature processing of stabilized compositions.

6 Claims, No Drawings

2-(2-HYDROXY-3,5-DI-TERT-OCTYLPHENYL)-2H-BENZOTRIAZOLE STABILIZED COMPOSITIONS

This is a continuation of application Ser. No. 6391, filed on Jan. 25, 1979, now abandoned.

BACKGROUND OF THE INVENTION

The present invention relates to selected 2-aryl-2H-benzotriazoles which are useful in protecting light-sensitive organic materials from deterioration and to stabilized compositions containing said benzotriazoles.

The UV-absorber of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 3,004,896; 3,055,896; 3,072,585; 3,074,910; 3,189,615 and 3,230,194.

However the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase compatibility and to reduce volatilization loss by modifying the structure of the benzotriazoles.

In U.S. Pat. No. 3,230,194, a higher alkyl group was substituted for methyl and the latter compound 2-(2-hydroxy-5-tert-octylphenyl)-2H-benzotriazole exhibited superior compatibility and performance in polyethylene compound to former.

Still other attempts were made to increase the compatibility of the aryl-2H-benzotriazole molecules in polymeric substrates and to decrease the tendency of said molecules to volatilize during processing and/or use by substituting the phenolic ring of said compounds with aralkyl groups such as benzyl, α-methylbenzyl and α,α-dimethylbenzyl radicals. Such compounds are disclosed in U.S. Pat. No. 4,127,586; Japanese Kokai 158588/75 and copending U.S. patent application No. 918,984.

Surprisingly, the instant compounds such as 2-(2-hydroxy-3,5-di-tert-octylphenyl)-2H-benzotriazole having only alkyl substitution on the phenolic ring of the benzotriazole exhibit an excellent combination of compatibility with and/or solubility in numerous polymeric substrates along with superior resistance to loss from stabilized compositions during high temperature processing or in end use applications where coatings or films of the stabilized compositions are exposed even to ambient weathering and light exposures compared to stabilized compositions containing the closest 2-aryl-2H-benzotriazoles of the prior art.

In U.S. Pat. No. 4,041,044, an improved process for making 2-aryl-2H-benzotriazoles is taught. In said Specification, a number of phenols and some twelve preferred phenols useful in said process are listed, inter alia 2,4-di-tert-octylphenol. Neither instant compound 2-(2-hydroxy-3,5-di-tert-octylphenyl)-2H-benzotriazole nor 5-chloro-2-(2-hydroxy-3,5-di-tert-octylphenyl)-2H-benzotriazole was exemplified nor prepared in said reference and the outstanding properties of these compounds now seen compared to other prior art benzotriazoles were not then recognized from among the myriad of possible compounds disclosed in this reference.

A dyeable stabilized polymer blend comprising polypropylene, a polyetherester, two phenolic antioxidants, a thiosynergist and 2-(2-hydroxy-3,5-dioctylphenyl)-2,1,3-benzotriazole is disclosed in U.S. Pat. No. 3,487,453. The exact chemical structure of the "dioctyl" substitution on the aryl-2H-benzotriazole moiety is not further identified nor can what influence or effect the benzotriazole exerted in this complex mixture of stabilizers in polypropylene be discerned.

DETAILED DISCLOSURE

This invention pertains to selected 2-aryl-2H-benzotriazole light absorbers and to organic materials, both polymeric and non-polymeric, stabilized thereby.

More particularly, the 2-aryl-2H-benzotriazoles of this invention are represented by the Formula I

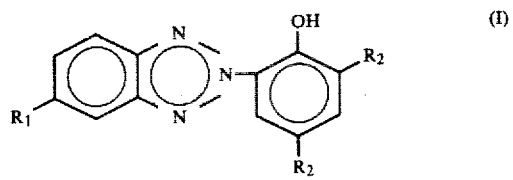

wherein
$R_1$ is hydrogen or chloro, and
$R_2$ is tert-octyl.
Preferably, $R_1$ is hydrogen.

The preferred compound is 2-[2-hydroxy-3,5-di-tert-octylphenyl]-2H-benzotriazole.

Synthesis of Compounds

The compounds of this invention are made by the following procedure:

Step I:

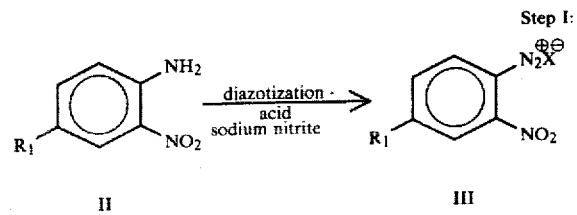

X is an anion such as chloride or sulfate.

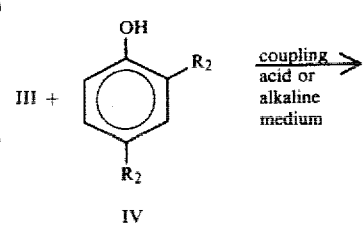

-continued

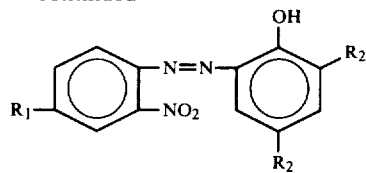

V

Step II:

V →(reductive cyclization)→

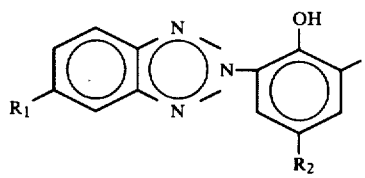

I $R_1$ and $R_2$ are as described earlier in the specification.

Step I is the coupling of a diazonium compound with a phenol and can be carried out under either acid or alkaline conditions. Preferably the coupling is carried out under acid conditions to give yields of coupled product, the o-nitroazobenzene intermediate (V) in the range of over 70% of theory.

Step II involves the reductive cyclization of the intermediate V to the corresponding 2-aryl-2H-benzotriazole. This can be conveniently carried out by a number of known reduction methods including zinc and alkali, hydrazine, and catalytic hydrogenation with noble metal or nickel catalysts for this reaction. Good yields of the 2-aryl-2H-benzotriazoles are obtained by using such systems.

The various starting materials, i.e., 2,4-di-tert-octylphenol, o-nitroaniline and 5-chloro-2-nitroaniline, are largely available as items of commerce or can easily be prepared by known methods.

The compounds of this invention are effective light stabilizers in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under 1), for example mixtures of polypropylene and polyethylene, polypropylene and polybutene-1, polypropylene and polyisobutylene.

3. Copolymers of the monomers based on the homopolymers cited under 1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under 5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.

9. Polymers which are derived fron unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

While compounds of this invention are very effective stabilizers for a host of organic substrates subject to light induced deterioration, as are the 2-aryl-2H-benzotriazole light absorbers in general, the instant compounds with their surprising resistance to loss from a stabilized composition during high temperature processing due to volatilization, exudation or sublimation have particular value in stabilizing polymeric substrated which are perforce processed at elevated temperatures.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof of polysulfones; of polyamides such as nylon-6, nylon-6,6, nylon 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

The instant compounds also provide excellent dye light stability to dyed polyamide and polyaramid fibers, such as nylon-6-6, nylon 6, poly(m-phenylene isophthalamide) fibers.

Four outstanding properties distinguish the instant compounds over the very close benzotriazoles of the prior art. These are:

1. lower volatility
2. greater solubility in common organic solvents used in polymer coating operations
3. greater compatibility in polyolefins, polyhydrocarbons, and other vinyl polymers
4. resistance to discoloration in the presence of some metal ions encountered in many polymer stabilizer or curing systems.

The practical and economic advantages flowing from each of these really unexpectedly better properties of the instant compounds compared to the prior are benzotriazoles are as follows:

a. Lower volatility, especially when combined with good polymer compatibility and/or solvent solubility, permits the instant benzotriazole compound to be incorporated into a polymer, to remain there even after high temperature processing, and to provide the ultimate fabricated product with desired light stabilization protection. If a stabilizer, no matter how effective it may be, is lost during processing, it cannot provide light protection to the fabricated product.

b. As can be seen in the table below, the instant compound of Example 1, 2-(2-hydroxy-3,5-di-tert-octylphenyl)2H-benzotriazole is appreciably more soluble in common organic solvents used in coating operations than close prior art compound TINUVIN 328, 2-(2-hydroxy-3,5-di-tert-amylphenyl)-2H benzotriazole.

| Solvent | Solubility Grams/100 ml solvent at 20° C. | |
|---|---|---|
| | Compound 1 (Example 2) | TINUVIN 328 |
| xylene | 56 | 44 |
| hexane | 35 | 16 |
| ethyl acetate | 35 | 16 |
| styrene | 67 | 40 |

The increased solubility of the instant compounds permits the preparation of more concentrated solids solutions of the instant compounds, reduces the volume of organic solvents to be handled (a major concern in environmental protection considerations as well as for economic reasons) and permits the practical use of less toxic solvents such as hexane in place of aromatic solvents.

c. Greater compatibility of the instant compounds in the polymeric substrates, coupled with reduced volatility discussed above, permits high temperature processing and high temperature use of stabilized products as well as extended ambient temperature use of said products. The undesirable exudation of a stabilizer onto processing equipment (causing frequent and costly premature equipment shutdowns) is prevented as well as exudation of the stabilizer (blushing) during use of the fabricated fiber or polymer. Such exudation is unsightly aesthetically, is costly in the premature loss of stabilizer and in the shortened product life of the fiber or polymer product from which the exuded stabilizer has escaped without exerting its desired function.

d. Surprisingly, the instant compounds exhibit resistance to discoloration with various metal ions encountered in many polymer stabilizer on curing systems. Many prior art benzotriazole compounds apparently form colored complexes of indeterminate structure with metal ions such as cobalt, iron, barium, cadmuim, tin and the like.

Polymer systems, such as unsaturated polyesters, alkyds, and the like wherein metal salts such as cobalt napthenate are used as dryers; poly(vinyl chloride) (PVC) or PVC copolymers stabilized with barium-cadmium or tin compounds; polyurethane systems containing tin catalysts; ABS resins containing iron impurities; represent substrates in which the instant benzotriazoles would have beneficial properties due to the apparent absence of complex formation between the instant benzotriazoles and said metal ions.

This is demonstrated by the Gardner color numbers for a xylene solution of various benzotriazole compounds before and after the addition of two drops of a 6% cobalt naphthenate solution (in xylene).

| Stabilizer* | Resistance to Discoloration Gardner Color Number** | |
|---|---|---|
| | Before | After adding Cobalt naphthenate |
| None | — | purplish color |
| Compound 1 (Example 2) | 1 | slight purplish color |
| TINUVIN 328 | 1 | 3.5 |
| TINUVIN P | 1 | 10 |
| UV 5411 | 1 | 10 |

*TINUVIN 328 = 2-(2-hydroxy3,5-di-tert-amylphenyl)-2H-benzotriazole.
TINUVIN P = 2-(2-hydroxy-5-methylphenyl)-2H-benzotrizole.
UV 5411 = 2-(2-hydroxy-5-tert-octylphenyl)-2H-benzotriazole.
**Gardner color number 1 is colorless (no yellow); 3.5 is perceptibly yellow; 10 (very yellow).

The discoloration caused by the apparent complexing of some benzotriazoles with various metal ions is often alone a sufficiently serious disadvantage to prevent the use of such benzotriazoles in any systems containing the metal ions. In other cases where the level of discoloration might be tolerated itself, the complex formation itself is disadvantageous by preventing the dryer from exercising its curing effects or the stabilizer from providing stabilization. In these cases, clearly the use of the prior art benzotriazoles would be counterindicated.

e. Finally in some thermoset acrylic resin systems crosslinked by melamine curing systems, curing is sometimes retarded by the presence of some prior art benzotriazoles. It is now seen that the instant benzotriazoles, presumedly due to some unexpected structural configuration around the hydroxyl group, do not interact with melamine curing agents in thermoset acrylic resin systems in contrast to some prior art benzotriazoles.

This is confirmed by comparing the pendulum hardness values of a thermoset acrylic resin film cured in the absence of any light stabilizer with the same resin films cured in the presence of 1% of a benzotriazole light stabilizer.

| Thermoset Acrylic Resin Film* Pendulum Hardness Values | |
|---|---|
| Stabilizer | Pendulum Hardness Value** After Curing (25 minutes at 140° C.) |
| None | 123 |
| TINUVIN 328 (1%)*** | 90 |
| Compound 1 (1%) (Example 2) | 126 |

*Resin is a styrene substituted acrylic copolymer crosslinked with an alkylated melamine curing system.
**The higher the number, the harder the coating.
***TINUVIN 328 is 2-(2-hydroxy-3,5-di-tert-amylphenyl)-2H-benzotriazole.

While the phenomenon is not understood, the instant benzotriazoles surprisingly do not retard or interfere with the curing of thermoset acrylic resin systems as witnessed by the retention or even enhancing of pendulum hardness values which are a direct measure of the amount and completeness of resin curing as sharply contrasted with a benzotriazole of the prior art having a closely related structure.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.1 to about 5% by weight of the stabilized composition, although this will vary with the particular substrate and application. An advantageous range is from about 0.3 to about 3%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension of emulsion of the stabilizer may be mixed with a solution, suspension, or emulsion of the polymer. The stabilized polymer compositions of the invention may optionally also contain from about 0.1 to about 5%, preferably from about 0.3 to about 3% by weight of various conventional additives, such as the following, particularly phenolic antioxidants or light-stabilizers, or mixtures thereof:

1. Antioxidants 1.1 Simple 2,6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylenebis-(6-tert.-butyl-4-ethylphenol), 4,4'-methylene-bis-(6-tert.-butyl-2-methylphenol, 4,4'-methylene-bis-(2,6-di-tert.-butylphenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example 2,4-bisoctylmercapto-6-(3,5-di-tert.-butyl-4-hydroxy-anilino)-s-triazine, 2-octylmercapto-4,6-bis-(3,5-di-tert.-butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5,-di-tert.-butyl-4-hydroxyphenyl-propionyl)-hexahydro-s-triazine and N,N'-di-3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenylpropionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propanediol, diethylene glycol thio-diethylene glycol, neopentylglycol, pentaerythritol, 3-thi undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pen bis-(2,2,6,6-tetramethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-trimethyl-1,3,8-triazaspiro[4.5]-decane-2,4-dione.

2.3 Oxalic acid diamides, e.g., 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bissalicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4-'bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

2-Nitro-2'-hydroxy-3',5'-di-tert-octylazobenzene

To a 5-liter, 3-necked flask fitted with a stirrer and thermometer was charged 317.3 grams of a 26% aqueous solution of technical naphthalenesulfonic acid, 6.7 grams of Triton X-207 (non-ionic surfactant), 19.6 grams of Conco AAS-90F (sodium dodecylbenzenesulfonate) and 315 ml of water. The mixture was warmed to 40° C. and then 393.6 grams of 2,4-di-tert-octylphenol was slowly added to the mixture with vigorous stirring keeping the temperature at 40° C.

A cold solution of o-nitroaniline diazonium chloride, prepared from 174.3 grams (1.26 mole) of o-nitroaniline and 87.1 grams (1.26 mole) of sodium nitrite in concentrated aqueous hydrochloric acid solution at a temperature of −5° to 0° C., was added dropwise into the reaction mixture over a 1.5-hour period. The resulting deep red to black reaction mixture was kept at 40° C. overnight. The temperature was raised to 65° C. for 1 hour; then the 95° for another 30 minutes. After cooling to 35° C., the reaction mixture was isolated as a fine dark red solid by filtration.

The crude product was triturated with 3.5 liters of water; then with 1400 ml of methanol and stirred in a blender, and filtered to yield a fine granular product. The dark red o-nitroazobenzene intermediate named above was obtained in a yield of 419.7 grams (72.7% of theory) and melted at 110°–112° C. Thin layer chromatography indicated a homogeneous product.

EXAMPLE 2

2-(2-Hydroxy-3,5-di-tert-octylphenyl)-2H-benzotriazole

To a 5-liter 3-necked flask fitted with a stirrer, thermometer, reflux condenser and nitrogen inlet was charged 400 grams (0.855 mol) of the o-nitroazobenzene intermediate of Example 1 and 1200 ml of toluene. To the resulting solution was added 260 ml of isopropanol and 260 ml of water. A nitrogen atmosphere was imposed and 175 ml of 50.1% aqueous sodium hydroxide was added. A flask containing 170.0 gram (2.6 gramatoms) of zinc was connected to the reaction flask by Gooch rubber tubing and the zinc dust was added portionwise to the reaction mixture over a 120-minute period. The zinc was added at such a rate to keep the internal temperature at 70° C. After the zinc was all added, an additional 30 ml of 50.1% sodium hydroxide and 20 grams of zinc were added to insure complete reaction. The reaction mixture was heated for 3 hours at 70° C. The mixture was cooled to room temperature by standing overnight and acidified with 500 ml of concentrated hydrochloric acid.

The zinc sludge was removed by filtration. The product was contained in the organic layer, which was washed with three 1000 ml portions of water, then 500 ml of saturated salt solution, and then dried over anhydrous sodium sulfate. The organic solvent was removed in vacuo to yield a crude product as a viscous syrup which crystallized on standing.

The crude product was recrystallized twice from 1000–1100 ml of ethanol to give 253 grams (67.8% of theory) of a pale yellow solid melting at 105°–106° C. of the above named compound. (Compound 1).

Analysis: Calcd for $C_{28}H_{41}N_3O$: C: 77.20; H,9.49; N:9.65. Found C: 77.22; H,9.14; N:9.77.

EXAMPLE 3

4-Chloro-2-nitro-2'-hydroxy-3',5'-di-tert-octylazobenzene

Coupling of 2,4-di-tert-octylphenyl with diazotized 4-chloro-2-nitroaniline using the procedure of Example 1 furnished the above-named compound as a deep red solid in 61.6% yield.

EXAMPLES 4

5-Chloro-2-(2-hydroxy-3,5-di-tert-octylphenyl)-2H-benzotriazole

When, using the general procedure of Example 2, the amount of 4-chloro-2-nitro-2'-hydroxy-3',5'-di-tert-octylazobenzene was substituted for 2-nitro-2'-hydroxy-3',5'-di-tert-octylazobenzene, the abovenamed compound was prepared in a yield of 71.8% as pale yellow crystals melting at 121°–122° C.

Analysis: Calcd for $C_{28}H_{40}ClN_3O$: C: 71.54; H,8.58; N:8.94. Found C: 71.26; H,8.46; N:9.03.

EXAMPLES 5

Resistance to Loss of Benzotriazole Stabilizers

A number of 2-aryl-2H-benzotriazole light stabilizers were subjected to thermal gravimetric analysis both isothermally at 280° C. to indicate the time in minutes to reach 10%, 50% and 100% weight loss of the stabilizer as well as in a scanning mode at a heating rate of 10°(C.) per minute to ascertain the temperature at which 10% and 50% weight loss of stabilizer were observed.

Experimental data are given on Table A.

These results correlate closely with the resistance of the indicated stabilizer to exudation or volatilization during any processing step with polymer formulations during the preparation of sheet, film, fiber or other fabricated pellicles. The absence or essential absence of exuded or volatilized stabilizer on processing equipment (i.e., rollers, guides, orifices, and the like) increases significantly the times between required shut-downs of continuously operated process equipment and represents enormous practical and economic savings related to the specific stabilizer used.

TABLE A

| | TGA Data | | | | |
|---|---|---|---|---|---|
| | Isothermal at 280° C. Time (minutes) to Indicated Weight Loss of Stabilizer | | | Scanning (at 10° C.) per minute Temperature °C. to Indicated Weight Loss of Stabilizer | |
| Stabilizer* | 10% | 50% | 100% | 10% | 50% |
| TINUVIN P | 0.4 | 0.75 | 1.2 | 182 | 215 |
| TINUVIN 350 | 0.6 | 1.0 | 1.8 | 210 | 247 |
| CYASORB UV-5411 | 0.6 | 1.9 | 3.5 | 225 | 260 |
| Compound 1 | 1.0 | 3.2 | 6.0 | 240 | 280 |

*TINUVIN P is 2-(2-hydroxy-5-methylphenyl)-2H-benzotriazole.
TINUVIN 350 is 2-(2-hydroxy-3-tert-butyl-5-sec-butylphenyl)-2H-benzotriazole.
CYASORB UV-5411 is 2-(2-hydroxy-5-tert-octylphenyl)-2H-benzotriazole.

Compound 1 (Example 2) clearly exhibits less volatility than the closest benzotriazole stabilizers. Compound 1 incorporated in a stabilized polymer composition would remain there during processing permitting excellent processability coupled with a final polymer pellicle with greater protection against subsequent light-induced deterioration.

EXAMPLE 6

Retention of Benzotriazole Stabilizers in Polycarbonate During Sheet Production

Polycarbonate (Lexan, General Electric) resin was formulated with 0.3% by weight of a number of 2-aryl-2H-benzotriazole light absorber stabilizers. The formulated resin was extruded at 600° F. (316° C.) into thin sheets. The resultant sheets were dissolved in methylene chloride and the polycarbonate precipitated with methanol. The amount of benzotriazole stabilizer retained in the polycarbonate sheet after fabrication was determined by gas chromatographic analysis.

The results are given on Table B.

TABLE B

| Stabilizer* | % Retained in Polycarbonate Sheet after Fabrication |
|---|---|
| TINUVIN 350 | 82 |
| CYASORB UV-5411 | 87 |
| Compound 1 | 100 |

*See Table A for chemical names of these stabilizers.

These data confirm the results on Table A that the instant Compound 1 resists loss by volatilization during processing.

EXAMPLE 7

Resistance to Loss During Cure and Weathering of Benzotriazole Stabilizers in Thermoset Acrylic Coatings Several thermoset acrylic resin and an alkyd/acrylic resin systems were formulated with 2% by weight of several benzotriazole light absorber stabilizers and cast onto glass plates at 1μ thick coatings. The coatings were then cured by heating at elevated temperatures for selected periods of time. The loss of benzotriazole light stabilizer was then ascertained by UV-absorption analysis of the coatings. Any decrease in absorbance of the coatings can be correlated to loss of benzotriazole stabilizer during the curing step.

These cured coatings were also subjected to the accelerated (quick) weathering test (QUV) involving alternating 4-hour period of UV irradiation at 60° C. with a 4-hour period of condensation (rain) at 50° C. for each cycle for a total of 670 hours. Again any decrease in absorbance of the weathered coatings can be correlated to loss of the benzotriazole stabilizer during the curing and weathering period.

Results are given on Table C.

alkyd resins and polycarbonates, stabilized with from 0.1 to 5% by weight of a compound of the formula

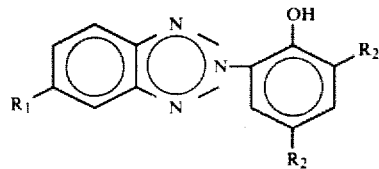

TABLE C

| | Absorbance Loss During Cure or Weathering (Percent) | | | | | | |
|---|---|---|---|---|---|---|---|
| | Thermoset Acrylic Resin Systems | | | | | Alkyd/Acrylic Resin | |
| | Single layer | | 2-Coat System | | High Solids | | |
| Stabilizer* | Heated 25 min at 120° C. | After Weathering | Heated 20 min at 135° C. | After Weathering | Heated 30 minutes at 150° C. | Heated 30 minutes at 125° C. | After Weathering |
| TINUVIN 328 | 25 | 35 | 59 | 69 | 95 | 77 | 100 |
| Compound 1 | 6 | 21 | 24 | 41 | 67 | 27 | 80 |

*TINUVIN 328 is 2-(2-hydroxy-3,5-di-tert-amylphenyl)-2H-benzotriazole.

As is seen from Table C, the instant compound exhibits far greater resistance to loss from the thermoset acrylic resin and alkyd/acrylic resin systems than did the close benzotriazole of the prior art. Compound 1 is discernibly less volatile than is TINUVIN 328 of closely related structure.

EXAMPLE 8

Stabilization of Polyethylene Terephthalate 0.5% of the compound of Example 2 is added as a stabilizer to molten polyethylene terephthalate at 270° C. with stirring under a nitrogen atmosphere. The resulting formulated polymer is ground with solid carbon dioxide.

The stabilized composition is extruded at elevated temperature into a film with little loss of stabilizer. The film is then exposed to actinic radiation. The stabilized film retains desirable physical properties for a longer period than does a film prepared from unstabilized polyester.

EXAMPLE 9

Stabilization of Polycarbonate

Polycarbonate (Lexan, General Electric) is mixed in a compounding extruder with 0.3% of the compound of Example 4. The stabilized composition is extruded into a sheet at elevated temperature with little loss of stabilizer. The sheet maintains physical properties after exposure to UV light for a longer period than does a sheet containing no stabilizer.

What is claimed is:

1. A composition of matter comprising an organic polymer, subject to light-induced deterioration, selected from the group consisting of thermoset acrylic resins, thermoplastic acrylic resins, alkyd/acrylic resins, alkyd resins and polycarbonates, stabilized with from 0.1 to 5% by weight of a compound of the formula wherein $R_1$ is hydrogen or chloro, and $R_2$ is tert-octyl.

2. A composition according to claim 1 wherein the organic polymer is selected from the group consisting of thermoset acrylic resins, thermoplastic acrylic resins and alkyd resins.

3. A composition according to claim 1 stabilized with 2-(2-hydroxy-3,5-di-tert-octylphenyl)-2H-benzotriazole.

4. A method of stabilizing an organic polymer, subject to light-induced deterioration, selected from the group consisting of thermoset acrylic resins, thermoplastic acrylic resins, alkyd/acrylic resins, alkyd resins and polycarbonates, which comprises incorporating in said material from 0.1 to 5% by weight of said material of a compound of the formula

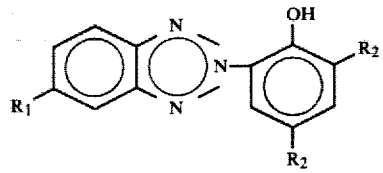

wherein $R_1$ is hydrogen or chloro, and
$R_2$ is tert-octyl.

5. A method according to claim 4 wherein the organic polymer is selected from the group consisting of thermoset acrylic resins, thermoplastic acrylic resins and alkyd resins.

6. A method according to claim 4 wherein the stabilizing compound being incorporated is 2-(2-hydroxy-3,5-di-tert-octylphenyl)-2H-benzotriazole.

* * * * *